(12) United States Patent
Kawashima et al.

(10) Patent No.: US 6,635,652 B1
(45) Date of Patent: Oct. 21, 2003

(54) AZAINDOLIZINONE DERIVATIVES AND CEREBRAL FUNCTION IMPROVERS CONTAINING THE SAME AS THE ACTIVE INGREDIENT

(75) Inventors: Seiichiro Kawashima, Ohizumi-machi (JP); Toshiyuki Matsuno, Ohizumi-machi (JP); Naoki Fukuda, Ohizumi-machi (JP); Kenichi Saitoh, Ohizumi-machi (JP); Yoshimasa Yamaguchi, Ohizumi-machi (JP); Masaya Higashi, Ohizumi-machi (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/030,159
(22) PCT Filed: Jul. 28, 2000
(86) PCT No.: PCT/JP00/05034
§ 371 (c)(1), (2), (4) Date: Jan. 30, 2002
(87) PCT Pub. No.: WO01/09131
PCT Pub. Date: Feb. 8, 2001

(30) Foreign Application Priority Data

Jul. 30, 1999 (JP) ............................................. 11/217002

(51) Int. Cl.[7] ................... A61K 31/437; A61K 31/438; C07D 471/04
(52) U.S. Cl. ........................ 514/278; 514/300; 546/18; 546/121
(58) Field of Search ................... 546/18, 121; 514/278, 514/300

(56) References Cited

U.S. PATENT DOCUMENTS

| 4,492,695 A | 1/1985 | Kaplan et al. |
| 4,514,415 A | 4/1985 | Wenk et al. |
| 4,760,083 A | 7/1988 | Myers et al. |

*Primary Examiner*—Patricia L. Morris
(74) *Attorney, Agent, or Firm*—Oblon, Spivak, McClelland, Maier & Neustadt, P.C.

(57) ABSTRACT

Azaindolizinon derivatives or pharmaceutically acceptable salts thereof represented by the formula I:

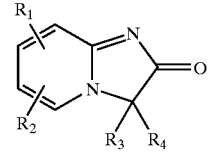

(I)

wherein $R_1$ represents hydrogen atom, halogen atom or $C_1$–$C_6$ alkyl, $R_2$ represents hydrogen atom, $C_1$–$C_6$ alkyl, $C_1$–$C_6$ alkoxy, hydroxy, halogen atom, amino, acetylamino, benzylamino, trifluoromethyl or —O—$(CH_2)_n$—$R_5$ ($R_5$ represents vinyl, $C_3$–$C_8$ cycloalkyl or phenyl, n being 0 or 1), $R_3$ and $R_4$ respectively represent $C_1$–$C_6$ alkyl or —CH($R_7$)—$R_6$ (wherein $R_6$ represents vinyl, ethynyl, phenyl (which may be substituted with $C_1$–$C_6$ alkyl, $C_1$–$C_6$ alkoxy, hydroxy, one or two halogen atoms, di $C_1$–$C_6$ alkylamino, cyano, nitro, carboxy or phenyl), phenethyl, pyridyl, thienyl or furyl and $R_7$ represents hydrogen atom or $C_1$–$C_6$ alkyl) or $R_3$ is coupled with $R_4$ to form indan or dihydrophenalene.

27 Claims, No Drawings

AZAINDOLIZINONE DERIVATIVES AND CEREBRAL FUNCTION IMPROVERS CONTAINING THE SAME AS THE ACTIVE INGREDIENT

TECHNICAL FIELD

The present invention relates to azaindolizinone derivatives or pharmacologically acceptable salts thereof, and cognitive enhancers comprising the azaindolizinone derivatives as effective components, represented by the formula I

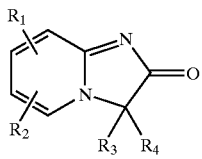

wherein $R_1$ represents hydrogen atom, halogen atom or $C_1$–$C_6$ alkyl, $R_2$ represents hydrogen atom, $C_1$–$C_6$ alkyl, $C_1$–$C_6$ alkoxy, hydroxy, halogen atom, amino, acetylamino, benzylamino, trifluoromethyl or —O—$(CH_2)_n$—$R_5$ (wherein $R_5$ represents vinyl, $C_3$–$C_8$ cycloalkyl or phenyl, n being 0 or 1), $R_3$ and $R_4$ respectively represent $C_1$–$C_6$ alkyl or —CH($R_7$)—$R_6$ (wherein $R_6$ represents vinyl, ethynyl, phenyl (which may be substituted by $C_1$–$C_6$ alkyl, $C_1$–$C_6$ alkoxy, hydroxy, one or two halogen atoms, di $C_1$–$C_6$ alkylamino, cyano, nitro, carboxy or phenyl), plienethyl, pyridyl, thienyl or furyl and $R_7$ represents hydrogen atom or $C_1$–$C_6$ alkyl) or $R_3$ is coupled with $R_4$ to form indan or dihydrophenalene.

More specifically, it relates to azaindolizinone derivatives useful as cognitive enhancers in connection with treatments on memory disturbance, memory acquirement and retention disturbance in, for example, senile dementia and Alzheimer's disease.

BACKGROUND ART

In recent years and with prolonged average life span, diseases such as senile dementia with memory disturbance present medically and socially great problems.

Dementia is a condition that cerebral functions once acquired have been continually disturbed into impairment in memory, decision and thinking, resulting in problems in ordinary social life. Alzheimer's disease, cerebrovascular dementia and mixture thereof amount to eight- or nine-tenths of underlying diseases for senile dementia, a core symptom of which is memory disturbance. Known with respect to Alzheimer's disease are the facts that the activity of choline acetyltransferase (ChAT), which is an acetylcholine sythesizing enzyme in the cerebral cortex, is lowered in comparison with normal control group of the same age [Bowen et al., Brain, 99, 459 (1976)] and that the nucleus basalis of Meynert, which is the nucleus of origin in cholinergic nerve of the cerebral cortex, is eminently exfoliated [Whitehouse et al., Science, 215, 1237–1239 (1982)]. Moreover, it is known, for example, that cognitive function in terms of mental test score is interrelated with lowering in activity of ChAT of the cerebral cortex [Perry et al., Br. Med. J. 25, 1457–1459 (1978)] and that scopolamine, which is a pharmacologically muscarinic receptor antagonist, will clinically cause amnesia [Drachman, Neurology, 27, 783–790 (1977)]. Set up against these backgrounds was a cholinergic hypothesis, where memory is deeply linked with cholinergic nerve function [Bartus et al., Science, 217, 408–417 (1982)]; nowadays, approaches based on cholinergic hypothesis have been made on development of medicines for treatment of senile dementia. Especially, experimental animal models with learning and memory disturbance induced by anti-cholinergic medicines (e.g., scopolamine) have been widely utilized in quest of medicines effective for learning and memory disturbance due to various causes of diseases (e.g., senile dementia including Alzheimer's disease).

Development of medicines effective against senile dementia has been strongly demanded; up to the present, antidementia medicines such as linopirdine, tacrine or aricept have been proposed and some of them have been marketed.

However, none of developed and marketed antidementia medicines are satisfactory for improvement and remedy of dementia symptom. There are still, therefore, strong demands on development of more effective antidementia medicines.

DISCLOSURE OF THE INVENTION

We, the inventors, who made devoted researches to pursue compounds having improved effects against cognitive dysfunction through central nervous system, especially cholinergic nervous system, found azaindolizinone derivatives of the formula I having significant antiamnesia effects against scopolamine-induced amnesia of rats, thus accomplishing the present invention.

The compounds of the present invention are represented by the formula I. The terms used for definition of letters in the formula will be defined and exemplified in the following.

The term "$C_1$–$C_6$" refers to a group having 1 to 6 carbon atoms unless otherwise indicated.

The term "$C_3$–$C_8$" refers to a group having 3 to 8 carbon atoms unless otherwise indicated.

The "$C_1$–$C_6$ alkyl" refers to a straight- or branched-chain alkyl group such as methyl, ethyl, n-propyl, isopropyl, n-butyl, tert-butyl, sec-butyl, n-pentyl or n-hexyl.

The "$C_1$–$C_6$ alkoxy" refers to a straight- or branched-chain alkoxy group such as methoxy, ethoxy, n-propoxy, isopropoxy, n-butoxy, tert-butoxy, sec-butoxy, n-pentyloxy, n-hexyloxy.

The "$C_3$–$C_8$ cycloalkyl" refers to cyclopropyl, cyclobutyl, cyclopentyl, cyclohexyl, cycloheptyl, cyclooctyl.

The "halogen atom" refers to fluorine, chlorine, bromine or iodine atom.

The compounds of the present invention may be as follows, though the present invention is not limited to these compounds.

3,3-dimethylimidazo[1,2-a]pyridin-2(3H)-one
3,3-dipropylimidazo[1,2-a]pyridin-2(3H)-one
3,3-dibutylimidazo[1,2-a]pyridin-2(3H)-one
3,3-diallylimidazo[1,2-a]pyridin-2(3H)-one
3,3-diallyl-8-benzyloxyimidazo[1,2-a]pyridin-2(3H)-one
3,3-di(2-propenyl)imidazo[1,2-a]pyridin-2(3H)-one
3,3-dibenzylimidazo[1,2-a]pyridin-2(3H)-one
3,3-dibenzyl-8-methylimidazo[1,2-a]pyridin-2(3H)-one
3,3-dibenzyl-5,7-dimethylimidazo[1,2-a]pyridin-2(3H)-one
3,3-dibenzyl-8-hydroxyimidazo[1,2-a]pyridin-2(3H)-one
3,3-dibenzyl-8-methoxyimidazo[1,2-a]pyridin-2(3H)-one
3,3-dibenzyl-8-ethoxyimidazo[1,2-a]pyridin-2(3H)-one
8-allyloxy-3,3-dibenzylimidazo[1,2-a]pyridin-2(3H)-one 3,3-dibenzyl-8-isopropoxyimidazo[1,2-a]pyridin-2(3H)-one
3,3-dibenzyl-8-cyclopropylmethyloxyimidazo[1,2-a]-pyridin-2(3H)-one
3,3-dibenzyl-8-cycloheptyloxyimidazo[1,2-a]pyridin-2(3H)-one
3,3-dibenzyl-6-chloroimidazo[1,2-a]pyridin-2(3H)-one
3,3-dibenzyl-6,8-dichloroimidazo[1,2-a]pyridin-2(3H)-one
3,3-dibenzyl-8-chloro-6-trifluoromethylimidazo[1,2-a]-pyridin-2(3H)-one
3,3-dibenzyl-8-benzyloxyimidazo[1,2-a]pyridin-2(3H)-one
8-amino-3,3-dibenzylimidazo[1,2-a]pyridin-2(3H)-one
8-acetylamino-3,3-dibenzylimidazo[1,2-a]pyridin-2(3H)-one
3,3-dibenzyl-8-benzylaminoimidazo[1,2-a]pyridin-2(3H)-one
3,3-bis(3-chlorobenzyl)imidazo[1,2-a]pyridin-2(3H)-one
3,3-bis(3-fluorobenzyl)imidazo[1,2-a]pyridin-2(3H)-one
3,3-bis(4-fluorobenzyl)imidazo[1,2-a]pyridin-2(3H)-one
3,3-bis(2,4-dichlorobenzyl)imidazo[1,2-a]pyridin-2(3H)-one
3,3-bis(4-dimethylaminobenzyl)imidazo[1,2-a]pyridin-2(3H)-one
3,3-bis(4-methoxybenzyl)imidazo[1,2-a]pyridin-2(3H)-one
3,3-bis(4-biphenylmethyl)imidazo[1,2-a]pyridin-2(3H)-one
3,3-bis(4-cyanobenzyl)imidazo[1,2-a]pyridin-2(3H)-one
3,3-bis(4-hydroxybenzyl)imidazo[1,2-a]pyridin-2(3H)-one
3,3-bis(3-phenyl-1-propyl)imidazo[1,2-a]pyridin-2(3H)-one
3,3-bis(2,4-difluorobenzyl)imidazo[1,2-a]pyridin-2(3H)-one
3,3-bis(4-nitrobenzyl)imidazo[1,2-a]pyridin-2(3H)-one
3,3-bis(4-carboxybenzyl)imidazo[1,2-a]pyridin-2(3H)-one
8-benzyloxy-3,3-bis(1-phenylethyl)imidazo[1,2-a]-pyridin-2(3H)-one
8-benzyloxy-3,3-bis(3-methylbenzyl)imidazo[1,2-a]-pyridin-2(3H)-one
8-benzyloxy-3,3-bis(4-methylbenzyl)imidazo[1,2-a]-pyridin-2(3H)-one
3-benzyl-3-(4-fluorobenzyl)imidazo[1,2-a]pyridin-2(3H)-one
3-ethyl-3-(4-fluorobenzyl)imidazo[1,2-a]pyridin-2(3H)-one
8-methyl-3,3-bis(3-pyridylmethyl)imidazo[1,2-a]-pyridin-2(3H)-one
8-methyl-3,3-bis(4-pyridylmethyl)imidazo[1,2-a]-pyridin-2(3H)-one
3,3-bis(2-thienylmethyl)imidazo[1,2-a]pyridin-2(3H)-one
3,3-bis(2-furylmethyl)imidazo[1,2-a]pyridin-2(3H)-one
spiro[imidazo[1,2-a]pyridin-2(3H)-one-3,2'-indan]
spiro[imidazo[1,2-a]pyridin-2(3H)-one-3,2'-[2,3] dihydrophenalene]

The compounds (I) of the present invention may have asymmetric carbon atoms in its structure. It is to be understood that isomers due to such asymmetric carbon atom or combination (racemate) of any of the isomers are included in the category of the compounds according to the present invention.

The compounds of the present invention may be in the form of acid addition salts as pharmaceutically acceptable salts. The appropriate acid addition salts which can be used include inorganic acid salts such as hydrochloride, sulfate, hydrobromide, nitrate and phosphate as well as organic acid salts such as acetate, oxalate, propionate, glycolate, lactate, pyruvate, malonate, succinate, maleate, fumarate, malate, tartrate, citrate, benzoate, cinnamate, methanesulfonate, benzenesulfonate, p-toluenesulfonate and salicylate.

Production Processes

The compounds of the present invention represented by the formula I are novel compounds and may be prepared in application of Kakei et al.'s method [Bulletin Chemical Society Japan, vol. 55, No. 11, 3590–3597 (1982)]. More specifically, as shown in the following reaction scheme, pyridinium bromide represented by the formula II as starting material is reacted with aralkyl halide represented by the formula III under the presence of base such as 1,8-diazabicyclo[5,4,0]-7-undecene, sodium ethoxide or sodium hydroxide.

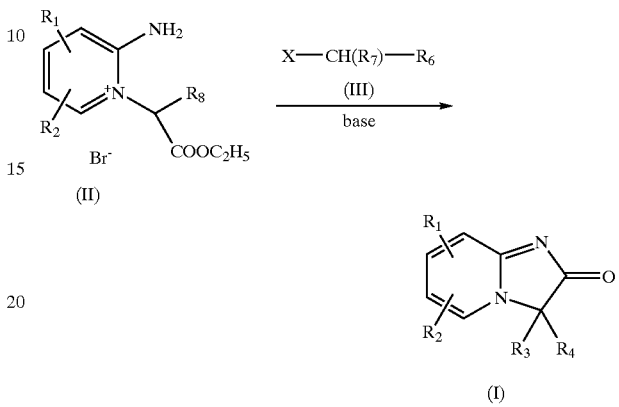

wherein $R_1$, $R_2$, $R_3$, $R_4$, $R_6$ and $R_7$ are as defined above and $R_8$ represents hydrogen atom, $C_1$–$C_6$ alkyl or benzyl, X represents halogen atom.

In this reaction, 2.0–2.2 moles of the compound III and 2–4 moles of the base are used per mole of the compound II when $R_8$ is hydrogen atom; and 1.0–1.2 mole of the compound III and 1–2 moles of the base are used per mole of the compound II when $R_8$ is not hydrogen atom. The reaction is made at the temperature of 0° C.–50° C. for 2–50 hours.

The solvent employed may be dimethylformamide (DMF), tetrahydrofuran (THF), acetonitrile, methanol or ethanol.

Thus obtained compounds of the present invention may be separated and purified according to an ordinary method such as extraction, condensation, neutralization, filtration, recrystallization or column chromatography.

Acid addition salts of the compounds of the present invention represented by the formula I may be prepared by various methods known in the art concerned. The appropriate acids used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

Pharmacological Effects

Next, pharmacological effects of the compounds of the present invention represented by the formula I will be described. The numbers of test compounds in Experiments 1) and 2) correspond to compound numbers in Examples referred to hereinafter. Comparative compounds used were the following antidementia compounds.

Compound A: linopirdine [3,3-bis(4-pyridylmethyl)-1-phenylindolin-2-one]
Compound B: tacrine [9-amino-1,2,3,4-tetrahydro-acridine]
Compound C: aricept [(R,S)-1-benzyl-4-(5,6-dimethoxy-1-indanon-2-yl)-methylpiperidine]

EXPERIMENT 1

Effects on Scopolamine-induced Amnesia (Through Oral Administration)

Male rats of the Strague Dawley strain at 8 weeks of age (260±2 g body weight) were used for evaluation through passive avoidance task. The apparatus of passive avoidance task comprises illuminated and dark chambers which are separated from each other by a wall with a door. Floors are constituted by grids made of stainless steel; only the grid in the dark chamber is furnished with wiring for electrification.

Effected on the first and second days of testing was preparative training; each rat was placed in the illuminated chamber and left for 3 minutes to habituate to the apparatus. On the third day of testing, the rats were individually placed in the illuminated chamber and after entering the dark chamber, the door was closed and the floor grid was electrified to deliver electric shock (100 V, 0.4 mA, a period of 0.8 sec). In order to induce amnesia, scopolamine hydrobromide (2 mg/kg) was intraperitoneally injected 20 minutes before the electric shock was delivered. Retention in memory on the electric shock was tested 24 hours later; more specifically, retention in passive avoidance trial was measured in terms of a time interval (latency) from placement of each rat in the illuminated chamber to its entry into the dark chamber. The latency over 300 seconds was recorded as 300 seconds. Respective test compounds were suspended in an aqueous solution of 1% carboxymethyl cellulose and orally administered at a dose of 0.01 or 1 mg/kg 60 minutes before the trial.

Antiamnesic effects of the test compounds were evaluated by inhibitory rate (%) which is calculated by the following formula:

$$\text{Inhibitory rate }(\%) = \frac{T(\text{treatment} + SC) - T(\text{placebo} + SC)}{T(\text{placebo}) - T(\text{placebo} + SC)} \times 100$$

wherein T stands for latency and SC stands for administration of scopolamine hydrobromide. Experimental results are shown in the following table in which, as to each of the test compounds, only the dose showing higher inhibitory rate was indicated.

TABLE 1

Effects on amnesia of rats induced by scopolamine

| Test compound | Dose (mg/kg. p.o.) | Inhibitory rate (%) |
| --- | --- | --- |
| Compound 1 | 1 | 50.4* |
| Compound 2 | 1 | 53.0** |
| Compound 3 | 1 | 47.4* |
| Compound 4 | 1 | 58.5** |
| Compound 5 | 1 | 34.8* |
| Compound 6 | 0.01 | 58.8* |
| Compound 8 | 0.01 | 34.8** |
| Compound 9 | 1 | 66.4** |
| Compound 10 | 0.01 | 78.7** |
| Compound 11 | 1 | 48.0** |
| Compound 13 | 0.01 | 57.0** |
| Compound 14 | 1 | 56.7** |
| Compound 16 | 0.01 | 55.4** |
| Compound 17 | 0.01 | 33.1 |
| Compound 18 | 1 | 58.7* |
| Compound 19 | 1 | 64.3** |
| Compound 20 | 0.01 | 30.2* |
| Compound 21 | 0.01 | 58.0** |
| Compound 22 | 0.01 | 37.4** |
| Compound 23 | 0.01 | 53.6* |
| Compound 24 | 0.01 | 56.8** |
| Compound 26 | 0.01 | 53.5** |
| Compound 27 | 0.01 | 60.7* |
| Compound 28 | 0.01 | 62.7* |
| Compound 29 | 1 | 114.6** |
| Compound 30 | 0.01 | 79.5* |
| Compound 31 | 1 | 60.4* |

TABLE 1-continued

Effects on amnesia of rats induced by scopolamine

| Test compound | Dose (mg/kg. p.o.) | Inhibitory rate (%) |
| --- | --- | --- |
| Compound 32 | 0.01 | 77.4* |
| Compound 34 | 0.01 | 59.6* |
| Compound 35 | 0.01 | 30.3 |
| Compound 36 | 0.01 | 30.0** |
| Compound 37 | 0.01 | 56.0** |
| Compound 38 | 1 | 58.5** |
| Compound 39 | 0.01 | 43.7* |
| Compound 40 | 1 | 40.7** |
| Compound 41 | 0.01 | 30.0* |
| Compound A | 0.01 | 8.8 |
|  | 1 | 20.9 |
| Compound B | 0.01 | 24.1 |
|  | 1 | 54.9** |
| Compound C | 0.01 | 12.5 |
|  | 1 | 24.7 |

**$P < 0.01$, *$P < 0.05$ (by Mann-Whitney U-test in comparison with scopolamine control group)

As is clear from the above results of Experiment 1, the compounds of the present invention exhibited greater antiamnesic effects than those of the known comparative compounds.

EXPERIMENT 2

Toxicity Test on Rats in a Single Dose Through Oral Administration

Used in the test were rats of the ICR strain at 6 weeks of age (27.9±0.4 g body weight). They were allowed to freely take food and water; however, fasting was made for a period of 17 hours before administration of the test compounds and for a period of 4 hours after the administration. The respective test compounds were suspended in 1% of hydroxypropyl cellulose (HPC) and orally administered. Until 6 hours after the administration of the test compounds, observation was made frequently, and after that once a day and totally for 14 days.

Used as the test compounds were Compounds 8 and 10. None of them induced death through oral administration of 2,000 mg/kg.

The compounds of the present invention represented by formula I are extremely advantageous in separating actions on the central and peripheral nerves and have no peripheral actions such as convulsion, salivation and diarrhea at a dose (0.01–10 mg/kg) showing antiamnesic effect on rat, and exhibit remarkable effects through oral administration. Therefore, they may be effective as cognitive enhancers for mammals including human.

The compounds of the present invention may be effective on diseases such as senile dementia, Alzheimer's disease, Parkinson's disease and other disorders of central nervous system and can be used for prevention or treatment for these diseases.

Next, described are ways, forms and amounts of administration in application of the compounds of the present invention to mammals, especially human.

The compounds of the present invention may be administered orally or parenterally. In oral administration, the compounds may be in the form of tablets, coated tablets, powders, granules, capsules, microcapsules, syrups and the like; and in parenteral administration, in the form of injections which may include soluble freeze-drying form, suppositories and the like. In the preparation of these forms, pharmacologically acceptable excipient, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range of from 0.1 to 50 mg and may be given in divided doses 1 to 3 times a day.

BEST MODE FOR CARRYING OUT THE INVENTION

The present invention is more specifically illustrated with reference to the following examples. It is to be, however, noted that the present invention is not limited to these.

EXAMPLE 1

3,3-Dibenzyl-8-isopropoxyimidazo[1,2-a]-pyridin-2(3H)-one (Compound 1)

Metallic sodium (81 mg) is added to 3.0 ml of absolute ethanol and is stirred for one hour at room temperature. Then, the reaction mixture was added with 586 mg (1.77 mmol) of 2-amino-3-isopropoxy-1-(ethoxycarbonylmethyl) pyridiniumbromide and stirred at room temperature for one hour. Then, the reaction mixture was added with 605 mg (3.54 mmol) of benzylbromide at 0° C. and stirred at room temperature for 4 hours. Then, the resulting precipitates were filtrated out and dried. The obtained crystals were re-crystallized from ethanol to obtain 588 mg (yield: 92%) of the titled compound.

Melting Point: 247–248° C.; NMR(CDCl$_3$) δ: 1.03 (6H, d, J=6 Hz), 3.15 (2H, d, J=14 Hz), 3.56 (2H, d, J=14 Hz), 4.60 (1H, sept., J=6 Hz), 6.48 (1H, t, J=7 Hz), 6.79 (1H, d, J=8 Hz), 6.9–7.2 (11H, m); MS m/z: 372 (M$^+$).

The following compounds were obtained from the corresponding starting materials and in a process similar to that in Example 1.

3,3-Dibenzyl-8-methoxyimidazo[1,2-a]pyridin-2(3H)-one (Compound 2)

Melting Point: 274–275° C.; NMR(CDCl$_3$) δ: 3.17 (2H, d, J=14 Hz), 3.56 (2H, d, J=14 Hz) 3.69 (3H, s), 6.49 (1H, t, J=7 Hz), 6.67 (1H, d, J=8 Hz), 6.9–7.2 (11H, m); MS m/z: 344 (M$^+$).

3,3-Dibenzyl-8-cyclopropylmethyloxyimidazo[1,2-a]-pyridin-2(3H)-one (Compound 3)

Melting Point: 236–237° C.; NMR(CDCl$_3$) δ: 0.12 (2H, q, J=5 Hz), 0.45 (2H, q, J=6 Hz), 0.99 (1H, m), 3.16 (2H, d, J=14 Hz), 3.55 (2H, d, J=14 Hz), 3.73 (2H, d, J=7 Hz), 6.47 (1H, t, J=7 Hz), 6.76 (1H, d, J=8 Hz), 7.0–7.2 (11H, m); MS m/z: 384 (M$^+$).

3,3-Dibenzyl-6-chloroimidazo[1,2-a]pyridin-2(3H)-one (Compound 4)

Melting Point: 246–248° C.; NMR(CDCl$_3$) δ: 3.16 (2H, d, J=14 Hz), 3.55 (2H, d, J=14 Hz), 6.70 (1H, d, J=10 Hz), 7.0–7.2 (12H, m); MS m/z: 348 (M$^+$).

8-Allyloxy-3,3-dibenzylimidazo[1,2-a]pyridin-2(3H)-one (Compound 5)

Melting Point: 214–215° C.; NMR(CDCl$_3$) δ: 3.16 (2H, d, J=14 Hz), 3.56 (2H, d, J=14 Hz), 4.4–4.5 (2H, m), 5.0–5.2 (2H, m), 5.7–5.9 (1H, m), 6.47 (1H, t, J=7 Hz), 6.74 (1H, d, J=8 Hz), 6.9–7.2 (11H, m); MS m/z: 370 (M$^+$).

3,3-Dibenzyl-8-benzyloxyimidazo[1,2-a]pyridin-2(3H)-one (Compound 6)

Melting Point: 240–241° C.; NMR(CDCl$_3$) δ: 3.17 (2H, d, J=14 Hz), 3.57 (2H, d, J=14 Hz), 5.03 (2H, s), 6.39 (1H, t, J=8 Hz), 6.65 (1H, d, J=8 Hz), 7.0–7.2 (16H, m); MS m/z: 420 (M$^+$).

8-Benzyloxy-3,3-bis(1-phenylethyl)imidazo[1,2-a]-pyridin-2(3H)-one (Compound 7)

Melting Point: 234–235° C.; NMR(CDCl$_3$) δ: 1.52 (6H, d, J=7 Hz), 3.51 (2H, q, J=7 Hz), 5.11 (2H, s), 6.14 (1H, t, J=7 Hz), 6.41 (1H, d, J=7 Hz), 6.63 (1H, d, J=8 Hz), 7.0–7.2 (15H, m); MS m/z: 448 (M$^+$).

3,3-Dibenzyl-8-methylimidazo[1,2-a]pyridin-2(3H)-one (Compound 8)

Melting Point: 262–263° C.; NMR(CDCl$_3$) δ: 2.05 (3H, s), 3.31 (2H, d, J=14 Hz), 3.56 (2H, d, J=14 Hz), 6.60 (1H, t, J=7 Hz), 6.9–7.2 (12H, m); MS m/z: 328 (M$^+$).

3,3-Dibenzyl-5,7-dimethylimidazo[1,2-a]pyridin-2(3H)-one (Compound 9)

Melting Point: 237–238° C.; NMR(CDCl$_3$) δ: 2.07 (3H, s), 2.80 (3H, s), 3.40 (2H, d, J=15 Hz), 3.71 (2H, d, J=15 Hz), 6.11 (1H, s), 6.34 (1H, s), 7.0–7.2 (10H, m); MS m/z: 342 (M$^+$).

3,3-Dibenzylimidazo[1,2-a]pyridin-2(3H)-one (Compound 10)

Melting Point: >300° C.; NMR(DMSO-D$_6$) δ: 3.39 (4H, s), 6.60 (1H, d, J=9 Hz), 6.8–7.2 (11H, m), 7.56 (1H, t, J=7 Hz), 8.75 (1H, d, J=7 Hz); MS m/z: 314 (M$^+$).

3,3-Dibenzyl-8-cyclopentyloxyimidazo[1,2-a]pyridin-2(3H)-one (Compound 11)

Melting Point: 268–269° C.; NMR(CDCl$_3$) δ: 1.4–1.7 (8H, m), 3.15 (2H, d, J=14 Hz), 3.55 (1H, d, J=14 Hz), 4.7–4.9 (1H, m), 6.47 (1H, t, J=7 Hz), 6.72 (1H, d, J=8 Hz), 6.9–7.2 (11H, m); MS m/z: 398 (M$^+$).

3,3-Dibenzyl-6,8-dichloroimidazo[1,2-a]pyridin-2(3H)-one (Compound 12)

Melting Point: 260–261° C.; NMR(CDCl$_3$) δ: 3.17 (2H, d, J=14 Hz), 3.55 (2H, d, J=14 Hz), 6.9–7.3 (11H, m), 7.41 (1H, d, J=2 Hz); MS m/z: 382 (M$^+$).

3,3-Dibenzyl-8-chloro-6-trifluoromethylimidazo[1,2-a]pyridin-2(3H)-one (Compound 13)

Melting Point: 234–236° C.; NMR(CDCl$_3$) δ: 3.22 (2H, d, J=14 Hz), 3.55 (2H, d, J=14 Hz), 6.9–7.0 (4H, m), 7.1–7.4 (7H, m), 7.51 (1H, d, J=2 Hz); MS m/z: 416 (M$^+$).

8-Benzyloxy-3,3-bis(3-methylbenzyl)imidazo[1,2-a]pyridin-2(3H)-one (Compound 14)

Melting Point: 233–235° C.; NMR(CDCl$_3$) δ: 2.20 (6H, s), 3.14 (2H, d, J=14 Hz), 3.48 (2H, d, J=14 Hz), 5.05 (2H, s), 6.38 (1H, t, J=7 Hz), 6.68 (1H, d, J=8 Hz), 6.7–7.3 (14H, m); MS m/z: 448 (M$^+$).

8-Methyl-3,3-bis(4-pyridylmethyl)imidazo[1,2-a]-pyridin-2(3H)-one (Compound 15)

Melting Point: 228–230° C.; NMR(CDCl$_3$) δ: 2.01 (3H, s), 3.13 (2H, d, J=14 Hz), 3.60 (2H, d, J=14 Hz), 6.60 (1H, t, J=7 Hz), 6.95 (4H, d, J=6 Hz), 7.22 (1H, d, J=7 Hz), 7.46 (1H, d, J=7 Hz), 8.40 (4H, d, J=6 Hz); MS m/z: 330 (M$^+$).

3,3-bis(4-Fluorobenzyl)imidazo[1,2-a]pyridin-2(3H)-one (Compound 16)

Melting Point: 290–292° C.; NMR(CDCl$_3$) δ: 3.13 (2H, d, J=14 Hz), 3.56 (2H, d, J=14 Hz), 6.62 (1H, t, J=7 Hz), 6.7–6.9 (5H, m), 6.9–7.1 (4H, m), 7.39 (1H, t, J=7 Hz), 7.52 (1H, brd, J=7 Hz); MS m/z: 350 (M$^+$).

3,3-bis(4-Dimethylaminobenzyl)imidazo[1,2-a]pyridin-2(3H)-one (Compound 17)

Melting Point: >300° C.; NMR(CDCl$_3$) δ: 2.86 (12H, s), 3.09 (2H, d, J=14 Hz), 3.37 (2H, d, J=14 Hz), 6.4–6.6 (5H, m), 6.7–6.9 (5H, m), 7.2–7.3 (1H, m), 7.37 (1H, t, J=7 Hz); MS m/z: 400 (M$^+$).

3,3-bis(3-Chlorobenzyl)imidazo[1,2-a]pyridin-2(3H)-one (Compound 18)

Melting Point: 271–272° C.; NMR(CDCl₃) δ: 3.14 (2H, d, J=14 Hz), 3.53 (2H, d, J=14 Hz), 6.66 (1H, t, J=7 Hz), 6.80 (1H, d, J=7 Hz), 6.9–7.2 (8H, m), 7.43 (1H, t, J=7 Hz), 7.51 (1H, brd, J=7 Hz); MS m/z: 382 (M⁺).

3,3-bis(4-Methoxybenzyl)imidazo[1,2-a]pyridin-2(3H)-one (Compound 19)

Melting Point: 248–251° C.; NMR(CDCl₃) δ: 3.66 (6H, s), 3.67 (2H, d, J=15 Hz), 4.00 (2H, d, J=15 Hz), 6.59 (4H, d, J=9 Hz), 6.93 (4H, d, J=9 Hz), 7.50 (1H, t, J=7 Hz), 6.71 (1H, d, J=7 Hz), 7.91 (1H, t, J=7 Hz), 9.78 (1H, d, J=7 Hz); MS m/z: 374 (M⁺).

3,3-bis(4-Biphenylmethyl)imidazo[1,2-a]pyridin-2(3H)-one (Compound 20)

Melting Point: >300° C.; NMR(CDCl₃) δ: 3.25 (2H, d, J=14 Hz), 3.62 (2H, d, J=14 Hz), 6.58 (1H, t, J=7 Hz), 6.77 (1H, d, J=7 Hz), 7.11 (4H, d, J=7 Hz), 7.3–7.6 (16H, m); MS m/z : 466 (M⁺).

3,3-bis(4-Cyanobenzyl)imidazo[1,2-a]pyridin-2(3H)-one (Compound 21)

Melting Point: 294° C. (decomposition); NMR(CDCl₃) δ: 3.19 (2H, d, J=14 Hz), 3.70 (2H, d, J=14 Hz), 6.6–6.8 (2H, m), 7.13 (4H, d, J=7 Hz), 7.43 (1H, t, J=7 Hz), 7.45 (4H, d, J=7 Hz), 7.62 (1H, brd, J=7 Hz); MS m/z: 364 (M⁺).

3,3-bis(4-Hydroxybenzyl)imidazo[1,2-a]pyridin-2(3H)-one (Compound 22)

Melting Point: 276.5–277.5° C.; NMR(CD₃OD-CDCl₃ (1:1)) δ: 3.62 (2H, d, J=14 Hz), 3.66 (2H, d, J=14 Hz), 6.58 (4H, d, J=9 Hz), 6.78 (4H, d, J=9 Hz), 7.17 (1H, d, J=7 Hz), 7.63 (1H, t, J=7 Hz), 8.12 (1H, t, J=7 Hz), 9.25 (1H, d, J=7 Hz); MS m/z: 346 (M⁺).

3,3-Diallylimidazo[1,2-a]pyridin-2(3H)-one (Compound 23)

Melting Point: 64–66° C.; NMR(CDCl₃) δ: 2.56 (2H, dd, J=9 Hz, J=14 Hz), 2.86 (2H, dd, J=6 Hz, J=14 Hz), 4.99 (2H, dd, J=1Hz, J=7 Hz), 5.04 (2H, d, J=1Hz), 5.4–5.6 (2H, m), 6.67 (1H, t, J=7 Hz), 7.17 (1H, d, J=7 Hz), 7.52 (1H, d, J=7 Hz), 7.59 (1H, d, J=7 Hz); MS m/z: 214 (M⁺).

Spiro[imidazo[1,2-a]pyridin-2(3H)-one-3,2'-indan] (Compound 24)

Melting Point: 206° C. (decomposition); NMR(CDCl₃) δ: 3.16 (2H, d, J=16 Hz), 3.89 (2H, d, J=16 Hz), 6.49 (1H, t, J=7 Hz), 7.1–7.2 (2H, m), 7.2–7.3 (4H, m), 7.61 (1H, t, J=7 Hz); MS m/z: 236 (M⁺).

3,3-Diallyl-8-benzyloxyimidazo[1,2-a]pyridin-2(3H)-one (Compound 25)

Melting Point: 160–162° C.; NMR(CDCl₃) δ: 2.54 (2H, dd, J=8 Hz, J=14 Hz), 2.86 (2H, dd, J=6 Hz, J=14 Hz), 4.96 (2H, dd, J=1Hz, J=5 Hz), 5.01 (2H, d, J=1Hz), 5.29 (2H, s), 5.4–5.6 (2H, m), 6.53 (1H, dd, J=7 Hz, J=8 Hz), 6.94 (1H, d, J=7 Hz), 7.16 (1H, d, J=8 Hz), 7.3–7.5 (5H, m); MS m/z: 320 (M⁺).

3,3-bis(3-Phenyl-1-propyl)imidazo[1,2-a]pyridin-2(3H)-one (Compound 26)

Melting Point: 227–228° C.; NMR(CDCl₃) δ: 0.9–1.1 (2H, m), 1.4–1.6 (2H, m), 1.6–1.8 (2H, m), 2.0–2.2 (2H, m), 2.3–2.5 (2H, m), 2.5–2.7 (2H, m), 6.61 (1H, t, J=7 Hz), 7.0–7.1 (4H, m), 7.1–7.3 (8H, m), 7.58 (1H, t, J=7 Hz); MS m/z: 370 (M⁺).

Spiro[imidazo[1,2-a]pyridin-2(3H)-one-3,2'-[2,3]dihydrophenalene] (Compound 27)

Melting Point: 262° C. (decomposition); NMR(CDCl₃) δ: 3.12 (2H, d, J=17 Hz), 3.98 (2H, d, J=17 Hz), 6.18 (1H, t, J=7 Hz), 6.48 (1H, d, J=7 Hz), 7.24 (1H, d, J=7 Hz), 7.34 (2H, d, J=7 Hz), 7.4–7.6 (3H, m), 7.86 (2H, d, J=7 Hz); MS m/z: 286 (M⁺).

3,3-bis(2,4-Difluorobenzyl)imidazo[1,2-a]pyridin-2(3H)-one (Compound 28)

Melting Point: 269–271° C.; NMR(CDCl₃) δ: 3.38 (2H, d, J=14 Hz), 3.47 (2H, d, J=14 Hz), 6.5–6.7 (3H, m), 6.7–6.8 (3H, m), 7.2–7.5 (3H, m), 7.6–7.7 (1H, m); MS m/z: 368 (M⁺).

3,3-Dipropylimidazo[1,2-a]pyridin-2(3H)-one (Compound 29)

Melting Point: 73–75° C.; NMR(CDCl₃) δ: 0.7–0.9 (8H, m), 1.1–1.3 (2H, m), 1.6–1.8 (2H, m), 2.0–2.2 (2H, m), 6.73 (1H, t, J=7 Hz), 7.19 (1H, d, J=7 Hz), 7.50 (1H, d, J=7 Hz), 7.63 (1H, t, J=7 Hz); MS m/z: 218 (M⁺).

3,3-bis(2-Thienylmethyl)imidazo[1,2-a]pyridin-2(3H)-one (Compound 30)

Melting Point: 289.5° C. (decomposition); NMR(CDCl₃) δ: 3.41 (2H, d, J=15 Hz), 3.70 (2H, d, J=15 Hz), 6.64 (1H, t, J=7 Hz), 6.7–7.0 (5H, m), 7.07 (2H, dd, J=1Hz, J=5 Hz), 7.38 (1H, d, J=7 Hz), 7.48 (1H, t, J=7 Hz); MS m/z: 326 (M⁺).

8-Acetylamino-3,3-dibenzylimidazo[1,2-a]pyridin-2(3H)-one (Compound 31)

Melting Point: 235–237° C.; NMR(CDCl₃) δ: 2.05 (3H, s), 3.20 (2H, d, J=14 Hz), 3.55 (2H, d, J=14 Hz), 6.61 (1H, t, J=7 Hz), 6.9–7.1 (4H, m), 7.1–7.2 (7H, m), 7.78 (1H, brs), 8.39 (1H, d, J=7 Hz); MS m/z: 371 (M⁺).

3,3-bis(2-Furylmethyl)imidazo[1,2-a]pyridin-2(3H)-one (Compound 32)

Melting Point: 205° C. (decomposition); NMR(CDCl₃) δ: 3.37 (4H, s), 6.11 (2H, d, J=3 Hz), 6.23 (2H, dd, J=2 Hz, J=3 Hz), 6.56 (1H, t, J=7 Hz), 6.97 (1H, d, J=7 Hz), 7.20 (2H, d, J=2 Hz), 7.22 (1H, d, J=7 Hz), 7.51 (1H, t, J=7 Hz); MS m/z: 294 (M⁺).

3,3-Dimethylimidazo[1,2-a]pyridin-2(3H)-one (Compound 33)

Melting Point: 200–202° C.; NMR(CD₃OD-CDCl₃ (1:1)) δ: 1.93 (6H, s), 7.72 (1H, t, J=7 Hz), 7.78 (1H, d, J=7 Hz), 8.50 (1H, t, J=7 Hz), 9.01 (1H, d, J=7 Hz); MS m/z: 162 (M⁺).

3,3-Dibutylimidazo[1,2-a]pyridin-2(3H)-one (Compound 34)

Melting Point: 100.5–102° C.; NMR(CDCl₃) δ: 0.6–0.9 (8H, m), 1.0–1.3 (6H, m), 1.6–1.8 (2H, m), 2.0–2.2 (2H, m), 6.71 (1H, t, J=7 Hz), 7.19 (1H, d, J=7 Hz), 7.50 (1H, d, J=7 Hz), 7.62 (1H, t, J=7 Hz); MS m/z: 246 (M⁺).

3,3-di(2-Propynyl)imidazo[1,2-a]pyridin-2(3H)-one (Compound 35)

Melting Point: 172–175° C.; NMR(CDCl₃) δ: 2.07 (2H, t, J=3 Hz), 2.80 (2H, dd, J=3 Hz, J=17 Hz), 3.08 (2H, dd, J=2.6 Hz, J=17 Hz), 6.75 (1H, t, J=7 Hz), 7.24 (1H, d, J=7 Hz), 7.69 (1H, t, J=7 Hz), 8.02 (1H, d, J=7 Hz); MS m/z: 210 (M⁺).

3,3-Dibenzyl-8-hydroxyimidazo[1,2-a]pyridin-2(3H)-one (Compound 36)

Melting Point: 283–285° C.; NMR(CDCl₃) δ: 3.20 (2H, d, J=14 Hz), 3.55 (2H, d, J=14 Hz), 6.58 (1H, t, J=7 Hz), 6.87 (1H, d, J=7 Hz), 6.9–7.0 (4H, m), 7.07 (1H, d, J=7 Hz), 7.1–7.2 (6H, m); MS m/z: 330 (M⁺).

3,3-Dibenzyl-8-benzylaminoimidazo[1,2-a]pyridin-2(3H)-one (Compound 37)

Melting Point: 250° C.; NMR(CDCl₃) δ: 3.42 (2H, d, J=14 Hz), 3.70 (2H, d, J=14 Hz), 4.35 (2H, d, J=6 Hz), 6.93 (1H, d, J=7 Hz), 7.0–7.3 (16H, m), 7.48 (1H, d, J=7 Hz), 8.66 (1H, brs); MS m/z: 419 (M⁺).

3,3-bis(4-Nitrobenzyl)imidazo[1,2-a]pyridin-2(3H)-one (Compound 38)

Melting Point: >300° C.; NMR(CD₃OD-CDCl₃ (1:1)) δ: 3.21 (2H, d, J=14 Hz), 3.67 (2H, d, J=14 Hz), 6.66 (1H, t, J=7 Hz), 6.75 (1H, d, J=7 Hz), 7.15 (4H, d, J=9 Hz), 7.39 (1H, t, J=7 Hz), 7.42 (4H, d, J=9 Hz), 7.56 (1H, d, J=7 Hz); MS m/z.: 404 (M$^+$).

8-Amino-3,3-dibenzylimidazo[1,2-a]pyridin-2(3H)-one (Compound 41)

Melting Point: 283–285° C.; MS m/z: 330 (M$^+$); NMR (CDCl$_3$) δ: 3.17 (2H, d, J=14 Hz), 3.53 (2H, d, J=14 Hz), 4.06 (2H, brs), 6.4–6.5 (2H, m), 6.94 (1H, t, J=7 Hz), 7.0–7.1 (4H, m), 7.1–7.2 (6H, m).

3,3-bis(4-Methoxycarbonylbenzyl)imidazo[1,2-a]pyridin-2 (3H)-one

Melting Point: 289–290° C.; NMR(CDCl$_3$) δ: 3.22 (2H, d, J=14 Hz), 3.66 (2H, d, J=14 Hz), 3.86 (6H, s), 6.60 (1H, t, J=7 Hz), 6.70 (1H, d, J=7 Hz), 7.0–7.1 (4H, m), 7.35 (1H, t, J=7 Hz), 7.50 (1H, d, J=7 Hz), 7.8–7.9 (4H, m); MS m/z: 430 (M$^+$).

EXAMPLE 2

3-Benzyl-3-(4-fluorobenzyl)imidazo[1,2-a]pyridin-2 (3H)-one (Compound 39)

630 mg (6.7 mmol) of 2-aminopyridine and 1.72 g (6.7 mmol) of ethyl 2-bromo-3-phenylpropionate were refluxed under heating in 50 ml of ether for 12 hours. The reaction mixture was allowed to cool to room temperature and ether was removed by decantation. The residue was added with and dissolved in 30 ml of absolute ethanol, which was added to a solution of 150 mg (6.5 mmol) of sodium in 10 ml of absolute ethanol and stirred at room temperature for one hour. Then, 0.8 ml (6.5 mmol) of 4-fluorobenzylbromide was added and stirred for overnight. The reaction mixture was added to ice water and extracted with methylene chloride. Then, the solvent was removed under reduced pressure and the residue was purified with silica gel column chromatography, thus obtaining 22 mg (yield: 1%) of the titled compound.

Melting Point: >300° C.; NMR(CDCl$_3$) δ: 3.12 (1H, d, J=14 Hz), 3.17 (1H, d, J=14 Hz), 3.54 (1H, d, J=14 Hz), 3.57 (1H, d, J=14 Hz), 6.59 (1H, t, J=7 Hz), 6.7–6.9 (3H, m), 6.9–7.1 (4H, m), 7.1–7.2 (3H, m), 7.3–7.5 (2H, m); MS m/z: 332 (M$^+$).

EXAMPLE 3

3,3-bis(4-Carboxybenzyl)imidazo[1,2-a]pyridin-2 (3H)-one (Compound 40)

300 mg (0.7 mmol) of 3,3-bis(4-methoxycarbonylbenzyl)-imidazo[1,2-a]pyridin-2(3H)-one prepared in the similar way to that of Example 1 was heated at 70° C. for 3 hours in a mixture of 8 ml of 2N-sodium hydroxide and 2 ml of ethanol. The reaction mixture was allowed to cool to room temperature and washed with methylene chloride. The water layer was adjusted by diluted hydrochloric acid to pH5 and the precipitated deposit was filtered out and dried, thus obtaining 200 mg (yield: 71%) of the titled compound.

Melting Point: >300° C.; NMR(DMSO-d$_6$) δ: 3.47 (2H, d, J=14 Hz), 3.54 (2H, d, J=14 Hz), 6.54 (1H, d, J=7 Hz), 6.84 (1H, t, J=7 Hz), 7.0–7.1 (4H, m), 7.51 (1H, t, J=7 Hz), 7.6–7.7 (4H, m), 8.70 (1H, d, J=7 Hz), 12.81 (2H, brs); FAB-MS m/z: 403[M+H]$^+$.

CAPABILITY OF EXPLOITATION IN INDUSTRY

The compounds according to the present invention are extremely advantageous in separating actions on the central and peripheral nerves and exhibit remarkable antiamnesic effect by administration to rats. Therefore, they may be applicable to improvement in cerebral function of mammals including humans and prevention and treatment of disorders of central nervous system such as senile dementia, Alzheimer's disease and Parkinson's disease.

What is claimed is:

1. A compound of formula (I) or a pharmaceutically acceptable salt thereof:

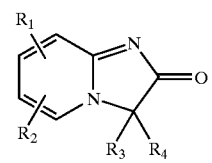

(I)

wherein

R$_1$ represents hydrogen atom, halogen atom, C$_1$–C$_6$ alkyl;

R$_2$ represents hydrogen atom, C$_1$–C$_6$ alkyl, C$_1$–C$_6$ alkoxy, hydroxy, halogen atom, amino, acetylamino, benzylamino, trifluoromethyl or —O—(CH$_2$)$_n$—R$_5$, wherein R$_5$ represents vinyl, C$_3$–C$_8$ cycloalkyl or phenyl and n is 0 or 1;

R$_3$ and R$_4$ each independently represent C$_1$–C$_6$ alkyl or —CH(R$_7$)—R$_6$, wherein R$_6$ represents vinyl, ethynyl, phenyl (which may be substituted with C$_1$–C$_6$ alkyl, C$_1$–C$_6$ alkoxy, hydroxy, one or two halogen atoms, di C$_1$–C$_6$ alkylamino, cyano, nitro, carboxy or phenyl), phenethyl, pyridyl, thienyl, furyl; and R$_7$ represents hydrogen atom or C$_1$–C$_6$ alkyl; or R$_3$ is coupled with R$_4$ to form indan or dihydrophenalene.

2. The compound of claim 1, wherein R$_3$ and R$_4$ are each independently selected from the group consisting of propyl, butyl, benzyl (which may be substituted with one or two fluorine atoms or cyano), furylmethyl and thienylmethyl.

3. The compound of claim 1, wherein R$_1$ and R$_2$ are both hydrogen atom and R$_3$ and R$_4$ are each independently selected from the group consisting of propyl and butyl.

4. The compound of claim 1, wherein R$_1$ and R$_2$ are both hydrogen atom and R$_3$ and R$_4$ are each benzyl (which may be substituted by one or two fluorine atoms or cyano).

5. The compound of claim 1, wherein R$_1$ and R$_2$ are both hydrogen atom and R$_3$ and R$_4$ are both benzyl.

6. The compound of claim 1, wherein R$_1$ and R$_2$ are both hydrogen atom and R$_3$ and R$_4$ are both furylmethyl.

7. The compound of claim 1, wherein R$_1$ and R$_2$ are both hydrogen atom and R$_3$ and R$_4$ are both thienylmethyl.

8. A pharmaceutical composition, comprising a compound of formula (I) or pharmaceutically acceptable salt thereof as claimed in claim 1 and a pharmnacologically acceptable excipient.

9. The compound of claim 1, wherein R$_1$ and R$_2$ are both hydrogen atom and R$_3$ is coupled with R$_4$ to form indan.

10. The compound of claim 1, wherein R$_1$ and R$_2$ are both hydrogen atom and R$_3$ is coupled with R$_4$ to form dihydrophenalene.

11. The composition of claim 8, wherein R$_3$ and R$_4$ are each independently selected from the group consisting of propyl, butyl, benzyl (which may be substituted with one or two fluorine atoms or cyano), furylmethyl and thienylmethyl.

12. The composition of claim 8, wherein R$_1$ and R$_2$ are both hydrogen atom and R$_3$ and R$_4$ are each independently selected from the group consisting of propyl and butyl.

13. The composition of claim 8, wherein R$_1$ and R$_2$ are both hydrogen atom and R$_3$ and R$_4$ are each benzyl (which may be substituted by one or two fluorine atoms or cyano).

14. The composition of claim 8, wherein $R_1$ and $R_2$ are both hydrogen atom and $R_3$ and $R_4$ are both benzyl.

15. The composition of claim 8, wherein $R_1$ and $R_2$ are both hydrogen atom and $R_3$ and $R_4$ are both furylmethyl.

16. The composition of claim 8, wherein $R_1$ and $R_2$ are both hydrogen atom and $R_3$ and $R_4$ are both thienylmethyl.

17. The composition of claim 8, wherein $R_1$ and $R_2$ are both hydrogen atom and $R_3$ is coupled with $R_4$ to form indan.

18. The composition of claim 8, wherein $R_1$ and $R_2$ are both hydrogen atom and $R_3$ is coupled with $R_4$ to form dihydrophenalene.

19. A method for enhancing cognitive function in a subject in need thereof, comprising administering an effective amount of a compound of formula (I) or a pharmaceutically acceptable salt thereof according to claim 1 to a subject in need thereof.

20. The method of claim 19, wherein $R_3$ and $R_4$ are each independently selected from the group consisting of propyl, butyl, benzyl (which may be substituted with one or two fluorine atoms or cyano), furylmethyl and thienylmethyl.

21. The method of claims 20, wherein $R_1$ and $R_2$ are both hydrogen atom and $R_3$ and $R_4$ are each independently selected from the group consisting of propyl and butyl.

22. The method of claim 21, wherein $R_1$ and $R_2$ are both hydrogen atom and $R_3$ and $R_4$ are each benzyl (which may be substituted by one or two fluorine atoms or cyano).

23. The method of claim 21, wherein $R_1$ and $R_2$ are both hydrogen atom and $R_3$ and $R_4$ are both benzyl.

24. The method of claim 21, wherein $R_1$ and $R_2$ are both hydrogen atom and $R_3$ and $R_4$ are both furylmethyl.

25. The method of claim 21, wherein $R_1$ and $R_2$ are both hydrogen atom and $R_3$ and $R_4$ are both thienylmethyl.

26. The method of claim 21, wherein $R_1$ and $R_2$ are both hydrogen atom and $R_3$ is coupled with $R_4$ to form indan.

27. The method of claim 19, wherein $R_1$ and $R_2$ are both hydrogen atom and $R_3$ is coupled with $R_4$ to form dihydrophenalene.

* * * * *

UNITED STATES PATENT AND TRADEMARK OFFICE
CERTIFICATE OF CORRECTION

PATENT NO.    : 6,635,652 B1
DATED         : October 21, 2003
INVENTOR(S)   : Seiichiro Kawashima et al.

It is certified that error appears in the above-identified patent and that said Letters Patent is hereby corrected as shown below:

<u>Column 14,</u>
Line 1, "Claims 20" should read -- Claim 19 --;
Lines 4, 7, 9, 11 and 13, "Claim 21" should read -- Claim 19 --.

Signed and Sealed this

Thirty-first Day of August, 2004

JON W. DUDAS
*Director of the United States Patent and Trademark Office*